United States Patent [19]

Jacobsen

[11] Patent Number: 4,986,980

[45] Date of Patent: Jan. 22, 1991

[54] WATER-SOLUBLE, CARRIER-BOUND PARAMAGNETIC METAL CONTAINING DIAGNOSTIC AGENTS

[75] Inventor: Trond Jacobsen, Oslo, Norway

[73] Assignee: Nycomed AS, Norway

[21] Appl. No.: 793,898

[22] Filed: Nov. 1, 1985

[30] Foreign Application Priority Data

Nov. 1, 1984 [SE] Sweden .................. 8405499

[51] Int. Cl.$^5$ .............................. A61K 49/00
[52] U.S. Cl. ........................ 424/9; 128/654;
128/653 R; 128/653 A; 436/173; 436/806;
534/15; 536/17.1; 536/51; 536/101; 536/112;
536/113; 536/121
[58] Field of Search ................. 424/9; 436/173, 806;
128/653, 654; 534/15; 536/17.1, 51, 101, 112,
113, 121

[56] References Cited

U.S. PATENT DOCUMENTS

| | | |
|---|---|---|
| 2,862,920 | 12/1958 | Berger et al. |
| 3,495,954 | 2/1970 | Grimes et al. |
| 3,563,978 | 2/1971 | Ochs |
| 3,928,581 | 12/1975 | Dahlberg et al. .............. 536/112 |
| 4,370,476 | 1/1983 | Usher et al. .................... 536/112 |
| 4,423,158 | 12/1983 | Porath ............................ 536/112 |
| 4,452,773 | 6/1984 | Molday |
| 4,615,879 | 10/1986 | Runge et al. ................... 424/9 |
| 4,675,173 | 6/1987 | Widder |
| 4,731,239 | 3/1988 | Gordon ........................... 424/9 |
| 4,822,594 | 4/1989 | Gibby |

FOREIGN PATENT DOCUMENTS

| | | |
|---|---|---|
| 8633082 | 1/1983 | Australia. |
| 0135125 | 8/1984 | European Pat. Off. |
| 0136812 | 8/1984 | European Pat. Off. |
| 0160552 | 4/1985 | European Pat. Off. |
| SE78/00001 | 6/1978 | PCT Int'l Appl. |
| US84/00020 | 1/1984 | PCT Int'l Appl. |
| SE84/00437 | 12/1984 | PCT Int'l Appl. |
| WO85/05554 | 12/1985 | PCT Int'l Appl. |
| 2137612A | 1/1984 | United Kingdom. |
| GR85/00234 | 5/1985 | United Kingdom. |

OTHER PUBLICATIONS

FIG. 3, Dextran Clearance ... (Thoren).
Structure of an Iron-Dextran Complex, "J. Pharm. Pharmac.", 1972, 24, pp. 513-517, Cox et al.
The Merck Index, 1976, pp. 2911.
High Resolution NMR, Academic Press 1980, Becker, pp. 48-51.
Work in Progress: Potential Oral and Intravenous Paramagnetic NMR Contrast Agents, Radiology, vol. 147, #3, p. 789, Ju. '83.

*Primary Examiner*—Richard L. Raymond
*Attorney, Agent, or Firm*—Bacon & Thomas

[57] ABSTRACT

There is disclosed a diagnostic agent containing a non-radioactive paramagnetic metal species which agent comprises a physiologically tolerable, water-soluble, hydroxyl group-containing macromolecular product to which is chemically bound said metal species, said product consisting essentially of at least one polymeric or polymerized carbohydrate or polymerized sugar alcohol or derivative thereof.

31 Claims, No Drawings

WATER-SOLUBLE, CARRIER-BOUND PARAMAGNETIC METAL CONTAINING DIAGNOSTIC AGENTS

The present invention relates to a diagnostic agent containing a paramagnetic metal species which diagnostic agent is for use in diagnosis based on NMR (Nuclear Magnetic Resonance) and ultrasound signals which are transformed into pictures over the examined area of a body of a human or non-human animal.

In NMR imaging the signal intensity (or contrast in the NMR picture) depends strongly on the nuclear density, the relaxation times and the parameters of the instrument (pulse sequence, frequency, etc.).

There are numerous methods of enhancing the contrast in NMR imaging, but many of these methods, such as manipulation of temperature, viscosity or other physical parameters, are not clinically usable. The use of paramagnetic compounds, however, which at small concentrations reduce the spin-lattice relaxation time ($T_1$) and at higher concentrations reduce the spin-spin relaxation time ($T_2$), appeared to be a favourable way to improve the contrast.

Diagnostic agents for use in NMR imaging and NMR in vivo spectroscopy have been reviewed by many authors, vide e.g. Sem. Nucl. Med., 13 (1983) 364, Radiology 147 (1983) 781 and J. Nucl. Med., 25 (1984) 506. These references primarily disclose inorganic paramagnetic salts but simple organic complexes are also mentioned.

Paramagnetic complexes for use in NMR diagnosis are also disclosed by EP-A-71564 and DE-A-3401052. These references describe chelate complexes formed from paramagnetic metal ions and various complex-forming agents containing organic nitrogen, phosphorus, oxygen and/or sulphur, primarily aminopolycarboxylic acids, e.g. ethylenediaminetetraacetic acid (EDTA) and diethylenetriaminepentaacetic acid (DTPA).

The toxicity of such chelate complexes is lower than that of contrast agents based on nonchelated paramagnetic metal ions, such as $Mn^{2+}$ and $Gd^{3+}$. However, the efficiency of such complexes of comparatively low molecular size is not improved considerably over that of inorganic paramagnetic salts.

Complexes comprising a paramagnetic metal species and a protein, such as an antibody, are disclosed by DE-A-3401052 and paramagnetic complexes bound to certain biomolecules such as proteins, hormones etc. are also discussed in EP-A-71564. In comparison with the above mentioned simple organic complexes of lower molecular size such complexes exhibit improved efficiency. However, the use of proteins is accompanied by several disadvantages.

Proteins are substances of very complicated structure and generally possess limited stability and applicability. Thus they are difficult to formulate into solutions and they should not be subjected to treatment by heat, which means that diagnostic agents containing proteins cannot be sterilized by the application of heat. The shelf life of such diagnostic agents will be limited and the proteins often exert an effect of their own which is not wanted in connection with the diagnostic investigation. The possibilities of choosing materials for different diagnostic purposes or materials with a desired way of excretion and a desired rate of elimination from the body of an animal (human or non-human) are also limited. Similar problems arise with the other biomolecules suggested as paramagnetic metal carriers in EP-A-71564.

It is an object of the present invention to provide a new diagnostic agent containing a paramagnetic metal species which diagnostic agent is more efficient than known low-molecular weight paramagnetic metal chelate containing diagnostic agents and more stable than known diagnostic agents containing water soluble protein- or other biomolecule-bound paramagnetic metal species.

We have now found that good levels of efficiency and stability can be achieved by using as a carrier for the paramagnetic metal species in a diagnostic agent a water-soluble macromolecular material comprising a polymeric or polymerized carbohydrate or a polymerized sugar alcohol or derivative thereof.

According to one aspect of the invention we therefore provide a diagnostic agent containing a non-radioactive paramagnetic metal species, characterized in that said agent comprises a physiologically tolerable, water-soluble, hydroxyl group-containing macromolecular product to which is chemically bound at least one non-radioactive paramagnetic metal species, said macromolecular product comprising at least one material selected from the group consisting of polymeric and polymerized carbohydrates and polymerized sugar alcohols and derivates thereof.

The present invention thus provides diagnostic agents containing a paramagnetic metal species, which diagnostic agents are based on well documented polymer compounds of simple structures and which, for instance, can easily be formulated, have a good shelf life and are well tolerable.

The present invention thus also provides diagnostic agents containing a paramagnetic metal species, the distribution and elimination of which diagnostic agents within the body under investigation can easily be varied by the use of polymers of different molecular weights and modified structures.

Hereinafter that part of the macromolecular product which comprises the polymeric or polymerized carbohydrate or polymerized sugar alcohol or derivative thereof will be referred to as "the basic molecule of the macromolecular product". The term "polymeric carbohydrate" is used herein to designate a naturally occurring polymer built up of carbohydrate monomers while the term "polymerized carbohydrate" is used to designate a synthetic polymer obtained by polymerizing carbohydrate molecules, e.g. with the aid of at least bifunctional coupling or cross-linking agents. Similarly, the term "polymerized sugar alcohol" is used to designate a synthetic polymer obtained by polymerizing sugar alcohol molecules, e.g. with the aid of at least bifunctional coupling or cross-linking agents. The term paramagnetic metal species as used herein includes within its scope both paramagnetic metal atoms and ions.

One of the advantages of the macromolecular product used according to the invention is that the molecular size of the macromolecules can easily be chosen to fit different needs in NMR and ultrasound examinations for diagnostic purposes. In general an average molecular weight ($\overline{M}_w$) of said product of at least 1000, preferably at least 3000, is chosen.

The physiologically tolerable, water-soluble, hydroxyl group-containing macromolecular product can, for instance, be based on a water-soluble cyclic or acyclic polysaccharide, such as a glucan, e.g. starch, amylose, amylopectin (including macromolecular dextrins thereof) glycogen, dextran and pullulan, or a fructan e.g. inulin and levan, cyclodextrine or another physiologically tolerable water-soluble polysaccharide of vegetable, microbial or animal origin.

Examples of polymerized carbohydrates or sugar alcohols which can be the basis of the macromolecular product of the present invention include so called polyglucose, which is obtained by polymerization of glucose, and water-soluble macromolecular products obtained by cross-linking carbohydrates or sugar alcohols (e.g. mannitol or sorbitol) with at least one bifunctional cross-linking agent, e.g. with epichlororhydrin, a diepoxide or a corresponding halogen hydrin or with a bifunctional acylating agent. An example of such a product which is commercially available is Ficoll (available from Pharmacia Fine Chemicals AB, Uppsala, Sweden - Ficoll is a registered Trade Mark) which is obtained by cross-linking sucrose with the aid of epichlorohydrin (vide e.g. SE-B-209018 and U.S. Pat. No. 3,300,474).

Further examples of substances which can form the basis of the macromolecular product according to the invention include water-soluble, physiologically tolerable derivatives of the polysaccharides mentioned above, for example hydroxyalkyl, carboxyalkyl, acyl or alkyl derivatives, e.g. hydroxyethyl, dihydroxypropyl, carboxymethyl, acetyl or methyl derivatives of said polysaccharides. Water-soluble derivatives of insoluble polysaccharides (e.g. of cellulose, for example for investigation of the gastrointestinal tract) are also of interest for this purpose.

Many substances contemplated as the basis of the macromolecular product are commercially available or extensively described in the literature. Fractions of the desired molecular weight may be obtained by conventional methods.

The macromolecular product is chosen according to the intended use of the diagnostic agent. Thus, for example, a product which is not degradable in the body may be chosen for investigation of body cavities having outward escape ducts, e.g. the gastrointestinal tract, the bladder and the uterus. Products which are not degradable in the body may also be used for parenteral administration, provided that the chosen molecular size of the macromolecules is sufficiently small as to allow excretion in the urine. Products which are degradable in the body to smaller excretable fragments may be chosen, for example, for parenteral administration when it is desirable that the molecular sizes of the macromolecules are so big that they are not excreted in the urine. For example, the macromolecules may be enzymatically degradable by hydrolases, e.g. endohydrolases, which hydrolyze glycosidic linkages in the macromolecules. For example, according to a particularly suitable embodiment of the invention macromolecules which are degradable by α-amylase are chosen. In this case macromolecules based on starch and other polysaccharides degradable by α-amylase and degradable derivatives thereof are used. However, the degree of substitution of such derivatives will not be chosen to be so high as to stop the derivative being degradable; generally the average degree of substitution will often be less than 0.6 and preferably will be less than 0.5 (i.e. less than one substituent per 2 glucose units), for example less than 0.3 or 0.2.

The macromolecules may be neutral or have a negative or positive net charge in solution. For parenteral use, macromolecules with no net charge or a negative net charge in solution are preferred. A negative net charge may be obtained for instance by introducing carboxyl groups or other negatively charged groups into the macromolecules if such groups are not already present in the macromolecules.

As mentioned above it is possible to choose the most suitable molecular size of the macromolecules for each diagnostic investigation to be performed. The molecular weight $\overline{M}_w$ may for example be within the range 1000 to 10000000, e.g. within the range 3000 to 1000000. For example, when it is desired that the macromolecules should be excreted (without any preceding degradation) with the urine after parenteral administration, the molecular weight is preferably less than 40000, for example less than 30000 or less than 20000 and, when it is desired that the macromolecules should not be rapidly excreted in the urine, the molecular weight is preferably higher than 40000, for example higher than 50000 or higher than 70000 or higher than 90000. For parenteral use, the molecular weight of the macromolecules is in most cases lower than 500000, for example lower than 300000 or lower than 200000 or lower than 100000 (e.g. within the range 1000 to 200000 or within the range 3000–100000). For administration to body cavities having external escape ducts, e.g. the bladder, the uterus and the gastrointestinal tract, a wide range of molecular weights can be chosen, for example molecular weights higher than 1000 and lower than 10000000, but in most cases higher than 3000 and lower than 1000000, for example within the range 5000 to 500000.

For administration to body cavities having external escape ducts (the gastrointestinal tract for example), it is possible to choose all the macromolecular products mentioned above, whereas for parenteral use for example macromolecules based on glucans having α-glycosidic linkages (e.g. starch, dextran or pullulan) or fructans having β-glycosidic linkages (e.g. inulin or levan) are especially preferred.

The non-radioactive paramagnetic metal is preferably selected from the group of elements having atomic numbers 21–29, 42, 44 and 57–70, elements having atomic numbers 24–29 or 62–69 being especially preferred. Examples of suitable lanthanides include gadolinium, europium, dysprosium, holmium and erbium. Examples of other suitable elements include manganese, iron, nickel, chromium and copper.

The paramagnetic metal species is chemically bound in the macromolecular product. The polymeric or polymerized carbohydrate or the polymerized sugar alcohol or derivative thereof used in the preparation of the diagnostic agent of the invention contains or is provided with binding structures to which the paramagnetic metal species may be bound. It is well known that many structures bind metals of the types which are of interest in this connection. Such structures are easily introduced into polymeric or polymerized carbohydrates or polymerized sugar alcohols or derivatives thereof if not already present in these macromolecules. For example, insoluble examples of such products have been used for extracting heavy metal ions from aqueous solutions and for binding metallic radionuclides. As it is desirable that the metal species is firmly bound to the macromolecular product, structures to which the metal species is bound in a complex can be used, structures wherein the metal species is bound in a chelate complex being preferred.

Many groups are known which bind metal ions in chelate complexes in which complexes the metal can be included e.g. in a 4-, 5- or 6-membered ring comprising said metal and two metal-coordinating atoms.

Preferably the chelate complex comprises at least two 5- or 6-membered rings comprising the metal, especially four to eight 5- or 6-membered rings. Such 5- and 6-membered rings comprise the metal and two metal-coordinating atoms, separated from each other by two or three atoms respectively.

According to another aspect, one of the metal-coordinating atoms is preferably a nitrogen atom and the other a nitrogen atom, a sulphur atom or an oxygen atom. The nitrogen atom can, for instance, be the nitrogen atom in an amino, imino or nitrilo group. The sulphur atom can, for instance, be the sulphur atom in a mercapto, thioether or thiono group. The oxygen atom can, for instance, be an oxygen atom in a keto, carboxylate, sulphonate, sulphate, phosphonate, phosphate, nitrate, hydroxyl or ether group. The metal coordinating atoms are members of chelate-forming groups which preferably contain at least two sequences, which may be equal or different, and which, in addition to the metal-coordinating atoms, preferably contain 2 or 3 carbon atoms (in the case of 5- and 6-membered rings respectively) in the chelate complex, one of the carbon atoms optionally being replaced by an oxygen, sulphur or nitrogen atom. For instance the chelate-forming groups may have the general formula

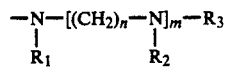

wherein n is 2 or 3, m is an integer 1, 2, 3 or higher, generally lower than 1000, e.g. lower than 100 or lower than 50 such as 1-50, or 2-6, and $R_1$, $R_2$ and $R_3$, which may be equal or different, each represents a hydrogen atom or a group $-CH_2-COOH$ or $-CH_2-CH_2-COOH$. The carboxymethyl and the carboxyethyl groups may be replaced by sulphomethyl, phosphomethyl or aminoethyl groups or by sulphoethyl, phosphoethyl or aminopropyl groups respectively, or by other equivalent groups. Furthermore the chelate-forming groups may of course be used in salt form.

The chelate-forming groups may be covalently bound to hydroxyl groups of the polymeric or polymerized carbohydrate or polymerized sugar alcohol or derivative thereof, e.g. by methods known per se. For instance, when using an aminopolycarboxylic acid, such as ethylenediaminetetraacetic acid (EDTA), diethylenetriaminepentaacetic acid (DTPA), triethylenetetraaminehexaacetic acid (TTHA) or N-hydroxyethylethylenediaminetriacetic acid (HEDTA), to establish chelate-forming groups, a carboxylic group of said acids may be utilised to produce an ester bond to the basic molecule of the macromolecular product by reaction, e.g. in the presence of a carbodiimide or another coupling agent. Anhydrides or acid halides of such polycarboxylic acids can also be used. Alternatively an aminopolycarboxylic acid containing a primary or secondary amino group can be reacted with a macromolecular substance containing carboxylic groups in order to form an amide bond, e.g. by using conventional methods for establishing such bonds.

Reactive groups may also be introduced into the basic molecule of the macromolecular product, e.g. a polysaccharide, for example in ways known per se; such reactive groups can then be reacted with thiol or amino groups or other nucleophilic moieties in the substance used for the introduction of chelate-forming groups. Examples of such groups are aldehyde and keto groups, halogenoacetyl, azide, isocyanate, isothiocyanate, s-triazinyl and divinylsulphone groups, carbonic acid ester groups, imidocarbonic acid ester groups (formed by cyanogen bromide activation), oxirane groups and groups which are easily converted to oxirane derivatives and reactive disulphides. On the other hand, activation of hydroxyl groups of the basic molecule of the macromolecular product with a base will enable a reaction with electrophilic moieties in the substance used for the introduction of chelate-forming groups to occur.

The complete chelate-forming group may be bound directly to the basic molecule of the macromolecular product or may be built up successively by binding a starting material for said group to said basic molecule and then modifying said starting material chemically. For instance, a compound of the general formula $H_2N-[(CH_2)_n-NH]_m-H$, wherein m and n are as defined above, may first be bound to said basic molecule, e.g. by methods known per se, whereafter the amino groups can be carboxymethylated or carboxyethylated to the desired extent.

If desired, a bridging group can be introduced between the chelate-forming groups and the basic molecule of the macromolecular product, e.g. in a manner known per se.

The paramagnetic metal can for example be bound to the macromolecular product by reacting the intermediate macromolecular substance containing chelate-forming groups with an excess of a water-soluble salt of the paramagnetic metal in aqueous solution at an appropriate pH-value, usually 2-7, e.g. 5-6. Purification and isolation of the product may then be performed e.g. by dialysis, ultrafiltration or precipitation and by filtration, evaporation or lyophilization respectively.

As mentioned above, the macromolecular product in solution may have a net charge, in which case the diagnostic agent should include a physiologically acceptable counterion. Examples of useful cations in this connection include sodium and potassium ions and the cations of non-toxic amines such as e.g. tris(hydroxymethyl)aminomethane, ethanolamine, diethanolamine and N-methylglucamine. Examples of useful anions include chloride ions and the anions of non-toxic organic acids.

The diagnostic agent according to the invention may e.g. be in the form of a solution in an aqueous medium or may be in dry form, e.g. in lyophilized form or as a powder or tablets, or in capsules. The tablets may be of the type which is dissolved in water before administration or the tablets may be of the type which is intended to be administered orally and be dissolved in the gastrointestinal tract, possibly with retarded dissolution. Where the agent contains the macromolecular product in solution, the solution may conveniently be contained in capsules or in liposomes.

For parenteral administration a solution in a sterile physiologically acceptable medium is preferably used, e.g. an isotonic aqueous solution. For administration to body cavities having external escape ducts (e.g. the gastrointestinal tract (for example by oral or rectal administration), the bladder and the uterus), a solution in a physiologically acceptable medium, e.g. an aqueous solution, optionally containing viscosity-increasing substances may conveniently be used. The aqueous solutions may be adjusted to the desired pH-value by means of a physiologically acceptable buffer.

Also other additives, such as those which are conventionally used within the pharmaceutical industry, can be added to the various different formulations; for instance, flavourants and dyestuffs can be incorporated into compositions for oral use. Thus it may be stated that the agents according to the present invention may conveniently be formulated to contain at least one pharmaceutical carrier or excipient and may optionally contain viscosity enhancing agents, osmolality regulators, colouring agents or flavouring agents.

The concentration of the paramagnetic metal in the diagnostic agent will be dependent on the administration form and on the particular organs or tissues to be studied. Generally the total dosage will be in the range of $10^{-6}$ to 10, preferably about $10^{-3}$ to $10^{-1}$, mmol of the paramagnetic metal species per kg bodyweight. The paramagnetic metal content of the macromolecular product will generally be 0.001–30 percent by weight, preferably more than 0.01 percent by weight, e.g. more than 0.1 percent by weight, and, for example, lower than 20 percent by weight or lower than 10 percent by weight calculated on the total weight of the macromolecular product in dry substance form.

The concentration of the macromolecular product in a solution to be used in NMR or ultrasound diagnosis will generally be higher than 0.01 percent by weight, for instance higher than 0.1 percent by weight, for example higher than 1 percent by weight, and lower than 35 percent by weight, for example lower than 25 percent by weight, e.g. lower than 15 percent by weight calculated on the total weight of the solution. For example, the concentration may conveniently be within the range 1–15 percent by weight calculated on the total weight of the solution.

The diagnostic agent according to the invention can be used in NMR imaging because the paramagnetic metal species bound to the macromolecular product reduces the relaxation times. It can also be used in NMR examinations due to its effect on the chemical shifts or it can be used in ultrasound examinations due to its effect on sound velocity.

According to a further aspect of the present invention we provide a method of diagnosis which method comprises administrering to a human or non-human animal body or to selected regions thereof contrast effective amounts of the diagnostic agent of the invention and generating an NMR or ultrasound image of said body or said region. We further provide a method of producing an image capable of use in diagnosis which method comprises administering to a human or non-human animal body or to a region thereof contrast effective amounts of the diagnostic agent of the invention and generating an NMR or ultrasound image of said body or said region, and optionally fixing said image in hardcopy form, e.g. in printed graphic or in photographic negative or positive form.

According to a yet still further aspect of the invention we provide a process for the preparation of a water-soluble paramagnetic metal species-containing macromolecular material comprising chemically binding a non-radioactive paramagnetic species to a physiologically tolerable, water-soluble, hydroxyl group-containing macromolecular product comprising at least one material selected from the group consisting of polymeric and polymerized carbohydrates and polymerized sugar alcohols and derivatives thereof, optionally following the chemical bonding to said macromolecular product of a chelate-forming group capable of complexing said paramagnetic metal species.

According to another aspect of the invention we provide a process for preparing a diagnostic agent containing a non-radioactive paramagnetic metal species, characterised in that said process comprises admixing with at least one pharmaceutical carrier or excipient a physiologically tolerable, water-soluble, hydroxyl group-containing macromolecular product to which is chemically bound at least one non-radioactive paramagnetic metal species, said macromolecular product comprising at least one material selected from the group consisting of polymeric and polymerized carbohydrates and polymerized sugar alcohols and derivatives thereof.

According to a still further aspect of the invention we provide the use for the manufacture of a diagnostic agent for use in a method of diagnosis practised on the human or animal body of a non-radioactive paramagnetic metal species and a physiologically tolerable, water-soluble, hydroxyl group-containing macromolecular product comprising at least one material selected from the group consisting of polymeric and polymerized carbohydrates and polymerized sugar alcohols and derivatives thereof.

The invention will now be further illustrated by the following non-limiting Examples. Percentages and ratios are by weight unless otherwise specified.

The following abbreviations are used in the Examples:

DMSO=dimethyl sulphoxide
DOTA=1,4,7,10-tetraazacyclododecane-N,N',N'',N'''-tetraacetic acid
DTPA=diethylenetriaminepentaacetic acid
DTPP=diethylenetriaminepentaphosphonic acid
EDTA=ethylenediaminetetraacetic acid
TTHA=triethylenetetraaminehexaacetic acid
SRRE=specific relaxation rate ($T_1$) enhancement
WS=solubility in water

EXAMPLE 1

1.0 g of triethylenetetraaminehexaacetic acid (TTHA) and 100 mg 4-dimethylaminopyridine were added to a solution of 2.0 g dextran with average molecular weight ($\overline{M}_w$) 40000 (Dextran T 40, from Pharmacia Fine Chemicals AB, Uppsala, Sweden) in dried dimethyl sulphoxide (DMSO). 1.9 g N-(3-dimethylaminopropyl)-N'-ethyl-carbodiimide hydrochloride were added and the solution was stirred for 22 hours at ambient temperature. Under the addition of 100 ml of distilled water the solution was cooled in an ice-water bath. The solution was stirred for 30 minutes and the pH-value was adjusted to 6.3. A solution of 0.40 g $MnCl_2.4H_2O$ in 20 ml distilled water was added. The pH-value was adjusted to 5.8 and the mixture was stirred for 30 minutes.

The solution was dialyzed against 0.9 per cent (w/v) NaCl until the external solutions were free from paramagnetic compounds (about 5 days), followed by dialysis with distilled water. The aqueous solution was evaporated and the product dried in vacuo at 50° C. 2.5 g of white flakes containing 0.25 per cent (w/w) Mn were obtained. Solubility in water (WS>50 mg/ml.

Specific relaxation rate enhancement (SRRE) was measured in a NMR proton spin analyzer (RADX Corp., Houston, Tex., U.S.A.) at 10 MHz in glycerol:water (1:2.13) (v:v) at 37° C.: 5.5 $s^{-1} mM^{-1}$.

EXAMPLE 2

1.0 g TTHA and 100 mg 4-dimethylaminopyridine were added to a solution of 2.0 g dextran $\overline{M}_w$ 40 000 (Dextran T 40, from Pharmacia Fine Chemicals AB, Uppsala, Sweden) in 200 ml dry DMSO. 1.9 g N-(3-dimethylaminopropyl)-N'-ethyl-carbodiimide hydrochloride were added and the solution was stirred for 22 hours at ambient temperature. Under the addition of 100 ml of distilled water the solution was cooled in an ice-water bath. The solution was sitrred for 30 minutes and the pH-value was adjusted to 6.3. A solution of 0.76 g $GdCl_3.6H_2O$ in 20 ml distilled water was added, the pH-value was adjusted to 5.8 and the mixture was stirred for 30 minutes. The product was purified and isolated as described in Example 1. 2.4 g of white flakes containing 1.0 per cent (w/w) Gd were obtained. WS>50 mg/ml. SRRE 9.0 $s^{-1} mM^{-1}$.

EXAMPLE 3

1.4 g of the bisanhydride of diethylenetriaminepentaacetic acid (DTPA), prepared from DTPA according to the method described in J. Pharm. Sci. 64, (1975) 704 by W. C. Eckelman et al. were added to a solution of 2.0 g dextran, $\overline{M}_w$ 70 000 (Dextran T 70, from Pharmacia Fine Chemicals AB, Uppsala, Sweden) in 100 ml dry DMSO with stirring at ambient temperature. The mixture was stirred at ambient temperature for 20 hours, cooled in an ice-water bath and 100 ml distilled water were gradually added. The ice-water bath was removed and the reaction mixture was stirred for 7 hours and the pH-value was adjusted to 6.5. A solution of 0.85 g $MnCl_2.4H_2O$ in 20 ml distilled water was added, the pH-value was adjusted to 5.7 and the solution was stirred for 30 minutes. The product was purified and isolated as described in Example 1. 3.0 g of white slightly yellow flakes containing 4.7 per cent (w/w) Mn were obtained. WS>50 mg/ml. SRRE 7.7 $s^{-1} mM^{-1}$.

EXAMPLE 4

DTPA was bound to dextran, $\overline{M}_w$ 70 000 (Dextran T 70, from Pharmacia Fine Chemicals AB, Uppsala, Sweden) as described in Example 3, resulting in a solution of DTPA-dextran.

A solution of 1.16 g $FeCl_3.6H_2O$ in 20 ml distilled water was added to the solution of DTPA-dextran at a pH-value of 6.5, the pH-value was adjusted to 5.7 and the solution was stirred for 30 minutes. The product was purified and isolated as described in Example 1. 4.0 g of light brown transparent flakes containing 4.6 per cent (w/w) Fe were obtained. WS>50 mg/ml. SRRE 5.0 $s^{-1} mM^{-1}$.

EXAMPLE 5

A solution of 1.80 g $GdCl_3.6H_2O$ in 20 ml water was added to a solution of 2.0 g dextran, $\overline{M}_w$ 70 000 (Dextran T 70, from Pharmacia Fine Chemicals AB, Uppsala, Sweden) in 100 ml distilled water at a pH-value of 5.8. The pH-value was adjusted to 5.8 and the solution was stirred for 30 minutes. The product was purified and isolated as described in Example 1. 1.7 g of colourless transparent flakes containing 0.7 per cent (w/w) Gd were obtained. WS>50 mg/ml. SRRE 0.2 $s^{-1} mM^{-1}$.

EXAMPLE 6

DTPA was bound to dextran, $\overline{M}_w$ 70 000 (Dextran T 70, from Pharmacia Fine Chemicals AB, Uppsala, Sweden) as described in Example 3, resulting in a solution of DTPA-dextran.

A solution of 1.6 g $GdCl_3.6H_2O$ in 20 ml distilled water was added to the solution of DTPA-dextran, the pH-value was adjusted to 5.7 and the solution was stirred for 30 minutes. The product was purified and isolated as described in Example 1. 3.2 g of colourless flakes containing 4.7 per cent (w/w) Gd were obtained. WS>50 mg/ml. SRRE 8.3 $s^{-1} mM^{-1}$.

EXAMPLE 7

3.0 g of diethylenetriaminepentaphosphonic acid (DTPP) prepared according to the method described in J. Org. Chem. 31 (1966) 1603 by K. Moedritzer and R. R. Orani were dissolved in 60 ml of water. 0.95 g of $Gd_2O_3$ was added and the mixture was refluxed for 3 hours. The mixture was cooled and the Gd-DTPP complex precipitated and was isolated by filtration and dried.

1.1 g of the dry complex and 100 mg of 4-dimethylaminopyridine were added to a solution of 2.0 g dextran $\overline{M}_w$ 70 000 (Dextran T 70, from Pharmacia Fine Chemicals AB, Uppsala, Sweden) in 200 ml dry DMSO. 2.5 g N-(3-dimethylaminopropyl)-N'-ethylcarbodiimide hydrochloride were added and the solution was stirred for 22 hours at ambient temperature. Under the addition of 100 ml of distilled water the solution was cooled in an ice-water bath. The product was purified and isolated as described in Example 1. 2.1 g of white flakes containing 1.0 per cent (w/w) Gd were obtained. WS>50 mg/ml. SRRE 0.9 $s^{-1} mM^{-1}$.

EXAMPLE 8

DTPA was bound to 2.0 g dextran, $\overline{M}_w$ 2.10$^6$ (Dextran T 2000, from Pharmacia Fine Chemicals AB, Uppsala, Sweden) as described in Example 3, resulting in a solution of DTPA-dextran.

A solution of 0.86 g $FeCl_2.4H_2O$ in 20 ml distilled water was added to the solution of DTPA-dextran at pH 6.5, the pH-value was adjusted to 5.7 and the solution was stirred for 30 minutes. The product was purified and isolated as described in Example 1. 3.3 g of yellow to brown flakes containing 3.6 per cent (w/w) Fe were obtained. WS>50 mg/ml. SRRE 2.0 $s^{-1} mM^{-1}$.

EXAMPLE 9

DTPA was bound to 2.0 dextran $\overline{M}_w$ 2.10$^6$ (Dextran T 2000, from Pharmacia Fine Chemicals AB, Uppsala, Sweden) as described in Example 3, resulting in a solution of DTPA-dextran.

A solution of 1.08 g $CuSO_4.5H_2O$ in 20 ml distilled water was added to the solution of DTPA-dextran at pH 6.5, the pH-value was adjusted to 5.7 and the solution was stirred for 30 minutes. The product was purified and isolated as described in Example 1. 3.5 g of blue flakes containing 5.2 per cent (w/w) Cu were obtained. WS>25 mg/ml. SRRE 0.6 $s^{-1} mM^{-1}$.

EXAMPLE 10

DTPA was bound to 2.0 g dextran, $\overline{M}_w$ 2.10$^6$ (Dextran T 2000, from Pharmacia Fine Chemicals AB, Uppsala, Sweden) as described in Example 3, resulting in a solution of DTPA-dextran.

A solution of 1.6 g $ErCl_3$ (containing 40 per cent of water) in 20 ml distilled water was added to the solution of DTPA-dextran at pH 6.5, the pH-value was adjusted to 5.7 and the solution was stirred for 30 minutes. The product was purified and isolated as described in Example 1. 3.1 g of rose coloured flakes containing 8.4 per cent (w/w) Er were obtained. WS>50 mg/ml. SRRE 0.05 $s^{-1}$ $mM^{-1}$.

EXAMPLE 11

100 g of dextran fractionated to $\overline{M}_w$ 80 000 were dissolved in a solution of 160 g sodium hydroxide and 2 g sodium borohydride in 500 ml of distilled water. 230 g of 2-chloroethylamine hydrochloride were added and the mixture was stirred with reflux on an oil bath at 120° C. for 22 hours. After cooling the mixture was neutralized to pH 7 with concentrated hydrochloric acid. The product was precipitated with ethanol, dissolved in 500 ml of distilled water and dialyzed. Reducing the volume by evaporation, precipitating with ethanol and drying in vacuo yielded 65 g of aminoethyldextran, $\overline{M}_w \sim$ 80 000, degree of substitution 0.35.

2.0 g aminoethyldextran were dissolved in 200 ml dry DMSO, 1.03 g of the bisanhydride of ethylenediaminetetraacetic acid (EDTA) prepared from EDTA according to the method described in J. Pharm. Sci. 64 (1975) 704 by W. C. Eckelman et al. were added and the mixture was stirred at ambient temperature for 16 hours. The mixture was cooled, 200 ml distilled water were added and the pH-value was adjusted to 5.8. After stirring at ambient temperature for 6 hours, a solution of 0.88 g $MnCl_2.4H_2O$ in 20 ml distilled water was added, pH was adjusted to 5.7 and the product was purified and isolated as described in Example 1. 3.8 g of white flakes containing 1.7 per cent (w/w) Mn were obtained. WS>50 mg/ml. SRRE 12.8 $s^{-1}$ $mM^{-1}$.

EXAMPLE 12

2.0 g aminoethyldextran (see Example 11) were dissolved in 200 ml dry DMSO, 1.3 g of the bisanhydride of DTPA were added and the mixture was stirred for 16 hours at ambient temperature. The mixture was cooled, 250 ml distilled water were added and the pH-value was adjusted to 5.8. After stirring at ambient temperature for 6 hours a solution of 1.47 $GdCl_3.6H_2O$ in 20 ml distilled water was added, the pH-value was adjusted to 5.0 and the product was purified and isolated as described in Example 1. 3.6 g of white solid containing 7.1 per cent (w/w) Gd were obtained. WS>50 mg/ml. SRRE 1.7 $s^{-1}$ $mM^{-1}$.

EXAMPLE 13

2.0 g of thioldextran (Dex-OOCCH$_2$CH(COOH)SH) $\overline{M}_w$ 70 000 and degree of substitution 0.16 (prepared by esterification of dextran with S-acetylmercaptosuccinic anhydride according to the method described in Bioinorg. Chem. 1 (1971) 65 by B. P. Garber and A. L. Fluharty) were dissolved in 200 ml distilled water. A solution of 0.42 g $CuSO_4.5H_2O$ in 50 ml distilled water was added at pH 6.0. When the addition was completed the pH-value was adjusted to 5.8. The product was purified, isolated and dried as described in Example 1. 1.85 g of dark green flakes containing 1.6 per cent (w/w) Cu were obtained. WS>25 mg/ml. SRRE 0.6 $s^{-1}$ $mM^{-1}$.

EXAMPLE 14

200 g dextran, $\overline{M}_w$ 70 000, (Dextran T 70, from Pharmacia Fine Chemicals AB, Uppsala, Sweden) were dissolved in 600 ml of distilled water. 600 ml of 40 per cent sodium hydroxide were added. 0.5 g sodium borohydride followed by 300 g chloroacetic acid was dissolved in the mixture at ambient temperature. A further portion of 24 g sodium hydroxide was dissolved in the mixture, which was left standing at ambient temperature for 2 hours. The mixture was neutralized with 30 per cent acetic acid and dialyzed. The product was precipitated with ethanol and dried in vacuo. 185 g of carboxymethyldextran sodium salt were obtained. $\overline{M}_w$ 65 000. Degree of substitution 0.11.

2.0 g of carboxymethyldextran sodium salt were dissolved in 100 ml distilled water at pH 5.8. 0.29 $FeCl_3.6H_2O$ in 20 ml distilled water was added and the pH-value was adjusted to 5.6 and the product was purified and isolated as described in Example 1. 1.9 g of brown transparent flakes containing 3.2 per cent (w/w) Fe were obtained. WS>50 mg/ml. SRRE 0.07 $s^{-1}$ $mM^{-1}$.

EXAMPLE 15

2.0 g of carboxymethyldextran sodium salt (see Example 14) were dissolved in 100 ml distilled water at pH 5.8. 0.40 g $GdCl_3.6H_2O$ in 20 ml distilled water was added, the pH-value was adjusted to 5.6 and the product was purified and isolated as described in Example 1. 1.75 g of colourless transparent flakes containing 2.8 per cent (w/w) Gd were obtained. WS>50 mg/ml. SRRE 0.2 $s^{-1}$ $mM^{-1}$.

EXAMPLE 16

2.0 g dextran phosphate, prepared by phosphorylation of dextran with $POCl_3$ according to the method described in U.S. Pat. No. 2,970,141, $\overline{M}_w$ 74 800 and degree of substitution 0.13, were dissolved in 200 ml distilled water. The pH-value was adjusted to 6.2 and a solution of 0.48 g $Eu(NO_3)_3.6H_2O$ in 20 ml distilled water was added. The pH-value was adjusted to 5.9 and an insoluble by-product removed by centrifugation and the water-soluble product purified and isolated as described in Example 1. 0.65 g of white colourless flakes containing 1.0 per cent (w/w) Eu was obtained. WS>50 mg/ml. SRRE 0.45 $s^{-1}$ $mM^{-1}$.

EXAMPLE 17

2.0 g dextran phosphate, prepared by phosphorylation of dextran with $POCl_3$ according to the method described in U.S. Pat. No. 2,970,141, $\overline{M}_w$ 74 800 and degree of substitution 0.13, were dissolved in 200 ml distilled water. The pH-value was adjusted to 6.2 and a solution of 0.40 g $GdCl_3.6H_2O$ in 20 ml distilled water was added. The pH-value was adjusted to 5.9 and an insoluble by-product removed by centrifugation and the water-soluble product purified and isolated as described in Example 1. 0.55 g of white flakes containing 3.1 per cent Gd was obtained. WS>50 mg/ml. SRRE 16 $s^{-1}$ $mM^{-1}$.

EXAMPLE 18

2.0 g of hydroxyethyl starch, prepared by hydroxyethylation of waxy starch with ethylene oxide according to the method described in U.S. Pat. No. 2,516,634, $\overline{M}_w$ 131 000 and degree of substitution 0.52, were dissolved in 60 ml of dry DMSO, 1.7 g of the bisanhydride of DTPA prepared as in Example 3 were added and the mixture was stirred at ambient temperature for 16 hours. Under the addition of 100 ml of distilled water the solution was cooled in an ice-water bath. The solution was stirred for 30 minutes and the pH-value was adjusted to 6.0. A solution of 1.23 g $NiCl_2.6H_2O$ in 20 ml of water was added, the pH-value was adjusted to 5.0 and the mixture was stirred at ambient temperature for 30 minutes. The starch derivative was purified and isolated as described in Example 1. 3.6 g of green flakes containing 8.5 per cent (w/w) Ni were obtained. WS>5 mg/ml. SRRE 0.01 $s^{-1} mM^{-1}$.

EXAMPLE 19

2.0 g of hydroxypropyl starch, prepared by hydroxypropylation of maize starch according to the method described in Stärke 23 (1971) 430 by D. C. Leegwater and J. B. Luten, $\overline{M}_w$ 49 000 and degree of substitution of 0.75, were dissolved in 100 ml dry DMSO, 1.03 g of the bisanhydride of EDTA (prepared as in Example 11) were added and the mixture was stirred at ambient temperature for 16 hours. The mixture was cooled and 100 ml distilled was added and the pH-value was adjusted to 6.2. After stirring at ambient temperature for 6 hours a solution of 1.79 g $GdCl_3.6H_2O$ in 20 ml distilled water was added, the pH-value was adjusted to 5.8 and the product was purified and isolated as described in Example 1. 3.4 of yellowish flakes containing 4.7 per cent (w/w) Gd were obtained. WS>50 mg/ml. SRRE 10.5 $s^{-1} mM^{-1}$.

EXAMPLE 20

2.0 g sodium carboxymethyl cellulose, $\overline{M}_w$ 90 000 and degree of substitution 0.8 (Blanose, available from Hercules Inc., Wilmington, Del., U.S.A. -Blanose is a registered Trade Mark) were dissolved in 200 ml distilled water, the pH-value was adjusted to 6.0 and a solution of 0.41 g $CuSO_4.5H_2O$ in 50 ml distilled water was added. The pH-value was adjusted to 5.2, the solution was stirred for 1 hour and the product was purified, isolated and dried as described in Example 1. 1.7 g of blue flakes containing 2.2 per cent (w/w) Cu were obtained. WS>25 mg/ml. SRRE 0.8 $s^{-1} mM^{-1}$.

EXAMPLE 21

2.0 g sodium carboxymethyl cellulose, $\overline{M}_w$ 90 000 and degree of substitution 0.8 (Blanose, available from Hercules Inc., Wilmington, Del., U.S.A.) were dissolved in 200 ml distilled water, the pH-value was adjusted to 5.6 and a solution of 160 mg $GdCl_3.6H_2O$ in 50 ml distilled water was added. The pH-value was adjusted to 5.2, the solution was stirred for 2 hours and the product was purified and isolated as described in Example 1. 1.4 g of white flakes containing 2.7 per cent (w/w) Gd were obtained. WS>50 mg/ml. SRRE 5.8 $s^{-1} mM^{-1}$.

EXAMPLE 22

7.0 g of the bisanhydride of DTPA were added to a solution of 10 g inulin (Sigma No. I-3754, available from Sigma Chemical Company, St. Louis, U.S.A. - Sigma is a registered Trade Mark) in 200 ml dry DMSO at ambient temperature. The mixture was stirred at ambient temperature for 20 hours followed by freeze drying of the solution. The solid material was redissolved in 250 ml distilled water, the solution was stirred overnight and the pH-value was adjusted to 5.0. A solution of 8.0 g $GdCl_3.6H_2O$ in 75 ml distilled water was added, the pH-value was adjusted to 5.5 and the solution was stirred for 1 hour. The mixture was subjected to ultrafiltration with 0.9 per cent (w/v) NaCl followed by distilled water. The aqueous solution was evaporated and the product dried in vacuo at 50° C. 13.1 g of a white solid containing 9.8 per cent (w/w) Gd were obtained. WS>50 mg/ml. SRRE 6.6 $s^{-1} mM^{-1}$.

EXAMPLE 23

2.0 g of a copolymer of sucrose and epichlorohydrin, $\overline{M}_w$ 70 000 (Ficoll 70, available from Pharmacia Fine Chemicals AB, Uppsala, Sweden) were dissolved in 200 ml dry DMSO. 1.03 g of the bisanhydride of EDTA were added and the mixture was stirred at ambient temperature for 16 hours. Under the addition of 100 ml distilled water, the reaction mixture ws cooled in an ice-water bath and the pH-value was adjusted to 5.8. A solution of 0.88 g $McCl_2.4H_2O$ in 20 ml distilled water was added. The pH was adjusted to 5.7 and the product was purified and isolated as described in Example 1. 2.8 g of white flakes containing 0.3 per cent (w/w) Mn were obtained. WS>50 mg/ml. SRRE 19.2 $s^{-1} mM^{-1}$.

EXAMPLE 24

EDTA was bound to 2.0 g of a copolymer of sucrose and epichlorohydrin, $\overline{M}_w$ 40 000 (Ficoll 400, available from Pharmacia Fine Chemicals AB, Uppsala, Sweden) as described in Example 23, resulting in a solution of EDTA-cross-linked sucrose. A solution of 1.4 g $FeCl_3.6H_2O$ in 20 ml distilled water was added, the pH was adjusted to 5.7 and the product was purified and isolated as described in Example 1. 3.2 g of brown flakes containing 2.7 per cent (w/w) Fe were obtained. WS>50 mg/ml. SRRE 0.5 $s^{-1} mM^{-1}$.

EXAMPLE 25

1,4,7,10-Tetraazacyclododecane-N,N',N'',N'''-tetraacetic acid (DOTA) was prepared according to the method described in Inorg. Chem., 19 (1980) 1319 by J. F. Desreux, and was reacted with glycine benzylester according to the mixed anhydride method described in Biochem. Biophys. Res. Comm., 77 (1977) 581, or the carbodiimide method described in Example 1 as follows: 12.8 g DOTA in dried DMSO was carefully added to a solution of 6.7 g N-(3-dimethylaminopropyl)-N'-ethyl-carbodiimide hydrochloride and 400 mg N,N-4-dimethylaminopyridine in DMSO. After 30 minutes a solution of 10.6 g of glycine benzylester-p-toluenesulphonate and 3.21 g of N-methylmorpholine was added dropwise during 1 hour. The solution was stirred for 22 hours and lyophilized. The residue was dissolved in water and washed several times with chloroform at pH 2 and 10. The resulting water solution was evaporated and the crude product washed with ethanol/water.

1.0 g DOTA-glycine-benzylester was dissolved in distilled water, to it were added 670 mg $GdCl_3$ and the mixture was warmed to 80° C. with stirring. The pH was adjusted to between 10 and 11 with NaOH and stirring was continued for 1 hour. After the cooling of the unclear solution, the pH was adjusted to 5-6 and the solution became clear. The solvent was evaporated and the residue taken up in dry DMSO. The product was bound to 2.0 g dextran, $\overline{M}_w$ 40000 (Dextran T40, available from Pharmacia Fine Chemicals AB, Uppsala, Sweden) as described in Example 1 for TTHA, and dialysed the way described therein. Lyophilization gave 2.1 g of a white voluminous product containing 1.9 per cent (w/w) Gd. WS>50 mg/ml, SRRE 16.8 $s^{-1} mM^{-1}$.

EXAMPLE 26

425 mg of gadolinium (III) DTPA-Dextran 40 were prepared in accordance with Example 6 and dissolved in 10 ml of an aqueous solution of 0.9 per cent NaCl.

The solution was sterile filtrated and filled in a 10 ml vial. The solution contained 2 mg Gd/ml.

EXAMPLE 27

200 mg of europium (III) dextran phosphate were prepared in accordance with Example 16 and dissolved in 100 ml distilled water. 2.0 g sodium carboxymethyl cellulose (Blanose, available from Hercules Inc., Wilmington, Del., U.S.A.) were also dissolved in this solution and the solution filled in a 100 ml bottle. The solution contained 20 μg Eu/ml.

EXAMPLE 28

306 mg of gadolinium (III) DTPA-inulin were prepared in accordance with Example 22 and dissolved in 10 ml of an aqueous solution of 0.9 per cent (w/v) NaCl. The solution was sterile filtrated and filled in a 10 ml vial. The solution contained 3 mg Gd/ml.

What is claimed:

1. A diagnostic agent comprising a water-soluble macromolecular complex of a non-radioactive paramagnetic metal ion, wherein said agent comprises a physiologically tolerable, water-soluble, hydroxyl group-containing macromolecular product of weight average molecular weight ($\overline{M}_w$) of at least 30,000 to which is bound in a coordination complex at least one said non-radioactive paramagnetic metal ion, said macromolecular product comprising at least one material selected from the group consisting of polysaccharides, polymerized sugar alcohols and derivatives thereof.

2. A diagnostic agent according to claim 1 wherein said macromolecular product is a material degradable in the animal body.

3. A diagnostic agent according to claim 1 wherein said macromolecular product is a material degradable by hydrolases.

4. A diagnostic agent according to claim 1 wherein said non-radioactive paramagnetic metal is selected from the group of elements having atomic numbers 21–29, 42, 44 and 57–70.

5. A diagnostic agent according to claim 4 wherein said non-radioactive paramagnetic metal is selected from the group consisting of gadolinium, erbium, europium, dysprosium, holmium, manganese, iron, nickel, chromium and copper.

6. A diagnostic agent according to claim 1 wherein said non-radioactive paramagnetic metal ion is bound to said macromolecular product in the form of a chelate complex.

7. A diagnostic agent according to claim 1 further comprising at least one pharmaceutical carrier or excipient.

8. A diagnostic agent according to claim 7 in solution form further comprising a viscosity enhancing agent and/or an osmolality regulator.

9. A diagnostic agent according to claim 1 wherein the molecular weight of said macromolecular product is sufficient to prevent rapid excretion of said paramagnetic metal ion from the blood into the urine, the weight average molecular weight of said macromolecular product being at least 40000.

10. A diagnostic agent according to claim 1 wherein the molecular weight of said macromolecular product is sufficient to prevent rapid excretion of said paramagnetic metal ion from the blood into the urine, the weight average molecular weight of said macromolecular product being at least 50000.

11. A diagnostic agent according to claim 1 wherein the weight average molecular weight of said macromolecular product is lower than 200000.

12. A diagnostic agent according to claim 1 wherein said macromolecular product comprises a polysaccharide material.

13. A diagnostic agent according to claim 1 wherein said macromolecular product comprises a material selected from dextrans, starches and derivatives thereof.

14. A diagnostic agent according to claim 5 wherein said paramagnetic metal is gadolinium.

15. A diagnostic agent according to claim 6 wherein said paramagnetic metal ion is bound in a chelate complex wherein one of the metal coordinating atoms is a nitrogen atom, one other being a nitrogen, oxygen or sulphur atom.

16. A diagnostic agent according to claim 6 wherein said paramagnetic metal ion is bound in a chelate complex by a chelate forming group which is itself bound to the basic molecule of the macromolecular product by a bridging group.

17. A diagnostic agent according to claim 6 wherein said paramagnetic metal ion is bound in a chelate complex by a chelate forming group which is a aminopolycarboxylic acid or a derivative thereof.

18. A diagnostic agent according to claim 16 wherein said chelate forming group is a aminopolycarboxylic acid or a derivative thereof.

19. A diagnostic agent comprising a water-soluble, macromolecular complex of a non-radioactive paramagnetic metal ion, wherein said agent comprises a physiologically tolerable, water-soluble, hydroxyl group-containing, macromolecular product to which is bound at least one said non-radioactive paramagnetic metal ion, said paramagnetic metal ion being complexed by diethylenetriamine-pentaacetic acid coupled to dextran of weight average molecular weight of about 40000 and said paramagnetic metal being gadolinium.

20. A diagnostic agent comprising a water-soluble, macromolecular complex of a non-radioactive paramagnetic metal ion, wherein said agent comprises a physiologically tolerable, water-soluble, hydroxyl group-containing, macromolecular product to which is bound at least one said non-radioactive paramagnetic metal ion, said paramagnetic metal ion being complexed by triethylene tetraaminehexaacetic acid coupled to dextran of weight average molecular weight of about 40000 and said paramagnetic metal being gadolinium.

21. A diagnostic agent comprising a water-soluble, macromolecular complex of a non-radioactive paramagnetic metal ion, wherein said agent comprises a physiologically tolerable, water-soluble, hydroxyl group-containing, macromolecular product to which is bound at least one said non-radioactive paramagnetic metal ion, said paramagnetic metal ion being complexed by diethylenetriamine-pentaacetic acid coupled to dextran of weight average molecular weight of about 70000 and said paramagnetic metal being gadolinium.

22. A diagnostic agent comprising a water-soluble, macromolecular complex of a non-radioactive paramagnetic metal ion, wherein said agent comprises a physiologically tolerable, water-soluble, hydroxyl group-containing, macromolecular product to which is bound at least one said non-radioactive paramagnetic metal ion, said paramagnetic metal ion being complexed by 1,4,7,10-tetraazacyclododecane-N,N',N", N'''-tetraacetic acid coupled by a glycine residue to dextran of weight average molecular weight of about 40000 and said paramagnetic metal being gadolinium.

23. A diagnostic agent according to claim 1 whereof the said paramagnetic metal ion has a specific relaxation rate, $T_1$, enhancement of at least $0.01 s^{-1}/mM$ of said paramagnetic metal ion measured at 10 MHz in a 1:2.13 by volume glycerol and water mixture at 37° C.

24. A diagnostic agent according to claim 6 wherein said chelate complex is uncharged on dissolution in a neutral aqueous medium.

25. A diagnostic agent according to claim 24, comprising Cu(II) bound in a chelate complex by the residue of S-acetylmercaptosuccinic acid coupled to thiol-dextran.

26. A diagnostic agent according to claim 24 comprising Gd(III) bound in a chelate complex by the residue of ethylenediaminetetraacetic acid coupled by hydroxypropyl starch.

27. A diagnostic agent according to claim 1 wherein said macromolecular product comprises at least one material selected from the group consisting of starches, alpha-amylase degradable polysaccharides and alpha-amylase degradable derivatives thereof having an average degree of substitution of less than 0.6.

28. A method of imaging a human or non-human animal body, which method comprises administering to a human or non-human animal body or to a selected region thereof a diagnostically effective amount of a diagnostic agent comprising a water-soluble macromolecular complex of a non-radioactive paramagnetic metal ion and generating an NMR or ultrasound image of said body or said region, wherein said agent comprises a physiologically tolerable, water-soluble, hydroxyl group-containing macromolecular product of weight average molecular weight ($\overline{M}_w$) of at least 30,000 to which is bound in a coordination at least one said non-radioactive paramagnetic metal ion, said macromolecular product comprising at least one material selected from the group consisting of polysaccharides, polymerized sugar alcohols and derivatives thereof.

29. A method of imaging according to claim 28 wherein the weight average molecular weight of said macromolecular product is at least 40,000.

30. A method of imaging according to claim 28 wherein said paramagnetic metal is gadolinium.

31. A method of imaging according to claim 29 wherein said paramagnetic metal is gadolinium.

* * * * *